United States Patent [19]
Armstrong et al.

[11] Patent Number: 6,099,469
[45] Date of Patent: Aug. 8, 2000

[54] REFLEX ALGORITHM FOR EARLY AND COST EFFECTIVE DIAGNOSIS OF MYOCARDIAL INFRACTIONS SUITABLE FOR AUTOMATED DIAGNOSTIC PLATFORMS

[76] Inventors: E. Glenn Armstrong, 498 Roxbury Rd., Stamford, Conn. 06902; Christoph Petry, 82 Town Green Dr., Elmsford, N.Y. 10523; Alan Wu, 11 Madison La., West Simsbury, Conn. 06092; Gerald Wagner, 970 Rte. 9N, Upper Grandview, N.Y. 10960

[21] Appl. No.: 09/088,870

[22] Filed: Jun. 2, 1998

[51] Int. Cl.$^7$ ...................................................... A61N 5/00
[52] U.S. Cl. ............................ 600/300; 128/920; 600/481
[58] Field of Search ..................................... 600/300, 301, 600/479, 481, 500, 504, 508, 509, 515, 518, 519, 513, 521, 544, 547; 128/900, 920, 925, 901, 924; 435/6, 91.2; 536/23.1

[56] References Cited

U.S. PATENT DOCUMENTS 5,690,103  11/1997  Groth et al. .
B1 5,747,274  8/1999  Jackowski ............................... 600/300

OTHER PUBLICATIONS

*Creation and Implementation of a Clinical Algorithm for Acute Myocardial Infarction*, Caragher, T.E., Fernandez B.B., Arnold M., Barr, L.A.; Clinical Chemistry, vol. 43, No. 6, p. S108, (1997).

*Early Assessment Of Patients With Suspected Acute Myocardial Infarction By Biochemical Monitoring And Neural Network Analysis*, Johan Ellenius, Torgny Groth, Bertil Lindahl and Lars Wallentin, Clinical Chemistry 43:10, pp. 1919–1925 (1997).

*Assessment Of Sensitive Thyrotropin Assays For An Expanded Role In Thyroid Function Testing: Proposed Criteria For Analytic Performance And Clinical Utility*; George G. Klee and Jan D. Hay, Journal of Clinical Endocrinology and Metabolism, vol. 64, No. 3, pp. 641–671 (1987).

*Use Of Neural Networks To Diagnose Acute Myocardial Infarction. II. A Clinical Application*, Susan M. Pedersen, Jorgen S. Jorgensen, J. Boiden Pederson, Clinical Chemistry vol. 42:4, pp. 613–617 (1996).

*Early Diagnosis And Exclusion Of Acute Myocardial Infarction Using Biochemical Monitoring*, Bertil Lindahl, Per Venge, and Lars Wallentin, Coronary and Heart Disease, vol. 6, pp. 321–328 (1995).

*Use Of An Artificial Neural Network For The Diagnosis Of Myocardial Infarction*, William G. Baxt, Annals of Internal Medicine, vol. 115, pp. 843–848 (1991).

*Early Diagnosis Of Myocardial Infraction By Timed Sequential Enzyme Measurements*, P. O. Collinson, S. B. Rosalki M. Flather, R. Wolman and T. Evans, Annals of Clinical Biochemistry, vol. 25, pp. 376–382 (1988).

*Analysis Of The Clinical Variables Driving Decision In An Artificial Neural Network Trained To Identify The Presence of Myocardial infraction*, William G. Baxt, Journal of the American College of Emergency Physicians and the Society for Academic Emergency Medicine, vol. 21, pp. 1439–1444 (1992).

(List continued on next page.)

*Primary Examiner*—Max Hindenburg
*Assistant Examiner*—Michael Astorino
*Attorney, Agent, or Firm*—Morgan & Finnegan, LLP

[57] ABSTRACT

A reflex algorithm for assessing cardiac patients, which does not require human decision-making in selecting assays to be performed. Performance of further biochemical marker tests on a patient is dependent upon the outcome of previously conducted tests. The reflex algorithm focuses on obtaining the most accurate test information as early as possible from several different tests run in very short intervals. The reflex algorithm may be implemented by a computer that can copy requests for the most appropriate test to the loadlists of automated clinical chemistry and immunoassay analyzers. Also provided is an integrated platform for executing clinical chemistry assays and immunoassays according to a reflex algorithm.

44 Claims, 7 Drawing Sheets

OTHER PUBLICATIONS

*Neural Network Analysis Of Serial Cardiac Enzyme Data, A Clinical Application Of Artificial Machine Intelligence*, James W. Furlong, Milton E. Dupuy and James A. Heinsimer, American Journal of Clinical Pathology, vol. 96, pp. 134–141 (1991).

*Prospective Evaluation Of An EDB–Based Diagnostic Program To Be Used In Patients Admitted To Hospital With Acute Chest Pain*, J. Jonsbu, O. Aase, A. Rollag, K. Liestol and J. Erikssen, European Heart Journal, vol. 14, pp. 441–446 (1993).

*Ruling Out Acute Myocardial Infarction, A Prospective Multicenter Validation Of A 12–Hour Strategy For Patients At Low Risk*, Thomas H. Lee, Gregory Juarex, E. Francis Cook, Monica C. Weisberg, Gregoary W. Rouan, Donald A. Brand and Lee Goldman, New England Journal Of Medicine, vol. 324, No. 18, pp. 1239–1246 (1991)

REFLEX ALGORITHM FOR EARLY AND COST EFFECTIVE DIAGNOSIS OF MYOCARDIAL INFRACTIONS SUITABLE FOR AUTOMATED DIAGNOSTIC PLATFORMS

FIELD OF THE INVENTION

The present invention relates generally to diagnostic methods and systems. More specifically, the invention pertains to a reflex algorithm for use in the early diagnosis of acute myocardial infarction. The algorithm of the present invention assists in the determination of the appropriate biochemical tests to be conducted on a given patient and alleviates unnecessary assays, and is well-suited for implementation on an automated diagnostic platform which integrates immunoassays and clinical chemistry assays.

BACKGROUND OF THE INVENTION

The contents of all patents, patent applications, published articles, books, reference manuals and abstracts cited hereinbelow are herein incorporated by reference in their entirety to more fully describe the state of the art to which the invention pertains.

Essential for the appropriate and optimal treatment and handling of patients who present with suspected myocardial infarction is an early diagnosis within the first hours after the onset of symptoms, e.g., chest pain, that are believed to be of cardiac origin. Although the 12-lead electrocardiogram (ECG) is usually immediately available, it is nondiagnostic on admission for the vast majority (e.g., up to about 60%) of patients. In cases with typical ST-segment elevations, the diagnosis of acute myocardial infarction (AMI) is straightforward. However, in those patients with a non-diagnostic ECG, a diagnosis according to World Health Organization (WHO) criteria can only be made by also considering the results of biochemical marker tests.

There has been interest in new biochemical markers for an early rule-in and rule-out of AMI. The diagnostic sensitivity and specificity of such markers may be high; however, they are often not sensitive enough for confirming or ruling out AMI immediately upon admission. It is a goal in the art to be able to identify at an early stage those patients, among the heterogeneous group of patients with chest pain, who have actually suffered an AMI, for hospital admission and early treatment, while ruling out the possibility of AMI in patients with non-AMI related chest pain to have them appropriately treated and discharged early from the emergency room.

To achieve some of the goals in the art, several methods have been proposed, such as diagnostic algorithms based on clinical data (T. H. Lee et al., 1991, *N. Eng. J. Med.*, 324:1239–1246; J. Jonsbu et al., 1993, *Eur. Heart J.*, 14:441–446) or biochemical markers (P. O. Collinson et al., 1988, *Ann. Clin. Biochem.*, 25:376–382; B. Lindahl et al., 1995, *Coron. Artery Dis.*, 6:321–328). In addition, artificial neural networks, based on clinical data including ECG (W. G. Baxt, 1991, *Ann. Intern. Med.*, 115:843–848; W. G. Baxt, 1992, *Ann. Emerg. Med.*, 21:1439–1444), biochemical markers (J. W. Furlong et al., 1991, Am. J. Clin. Pathol., 96:134–141; S. Pedersen et al., 1996, *Clin. Chem.*, 42:613–617) and frequent sampling and measurement of selected markers of AMI (J. Ellenius et al., 1997, *Clin. Chem.*, 43:1919–1925) have been used as an alternative technique in AMI diagnosis.

Reflex algorithms (i.e., algorithms which specify selection of subsequent tests based on results of previous tests, without the need for subjective human decision-making in selecting tests) have been employed in the areas of clinical chemistry and laboratory medicine for more than a decade. Initially, such algorithms were suggested for the assessment of thyroid disease, where an assay for thyroid stimulating hormone (TSH) was the first-line test, and further markers were chosen, or omitted, on the basis of the TSH result (J. Klee, 1987, *J. Clin. Endocrinol.*, 64:641–671). To date, thyroid testing is the only area in laboratory medicine in which reflex testing has found acceptance among practitioners in the art. Reflex algorithms for the detection of other disease states and medical conditions are not conventionally employed. Thus, reflex testing and the use of algorithms for the diagnosis of other diseases are needed in the art and promise to improve the diagnostic process through their efficiency, effectiveness and reduction of costs of further unwarranted testing.

An abstract by T. E. Caragher et al. (1997, *Clin. Chem.*, 43:S108) discloses serial measurements of several AMI markers at defined time points. The criteria for confirmation of AMI were defined based on the results of the testing algorithm. The algorithm of Caragher et al. is not a reflex algorithm, because subsequently ordered tests do not depend on the previous results obtained.

J. Ellenius et al. disclosed a computer assisted approach to diagnose acute myocardial infarctions. In this report, creatine kinase isoforms, myoglobin and Troponin T were measured in short time intervals and the diagnosis was made by processing the results using a neural network. Such a neural network is not performed in the manner of reflex testing and does not try to minimize the number of necessary tests. Instead, it focuses on obtaining the most accurate information as early as possible from several different tests run in very short intervals.

It is appreciated, therefore, that there is a need for further improvements and developments in detecting myocardial infarction, and more particularly, for a reflex method for specific and sensitive detection of AMI.

SUMMARY OF THE INVENTION

The present invention overcomes the above, and other, limitations of the prior art and the background art by providing a method and system for detecting myocardial infarction in an individual according to a hierarchical ordering of biochemical marker measurement steps in which subsequent biochemical marker measurements are selectively performed based on the results of previous biochemical marker measurements and without the need for human decision making. In accordance with an aspect of the present invention, a method for detecting myocardial infarction in an individual includes performing one of a plurality of sequences of biochemical marker measurement steps prescribed by a decision tree, each of the biochemical marker measurement steps including measuring a concentration level of at least one biochemical marker of myocardial infarction in a serum, plasma or whole blood sample obtained from the individual at one of a plurality of times from admission. Each sequence of the decision tree begins with a common first biochemical marker measurement step conducted on a first serum, plasma or whole blood sample obtained from the individual within a first predetermined time from admission. Each of the biochemical marker measurement steps subsequent to the common first step is selectively performed based on results from a precedent biochemical marker measurement step, each sequence terminating in a respective final biochemical marker measurement step conducted on serum, plasma, or whole blood sampled from the individual at one of a plurality of different times subsequent to admission. In addition to other clinical data, an indication of myocardial infarction is provided for the individual based on the sequence of biochemical marker measurement steps performed and on the results of the final biochemical marker measurement step.

In accordance with another aspect of the present invention, an illustrative AMI detection reflex algorithm, which establishes useful biochemical tests for patients with suspected myocardial infarction, begins with the step of testing myoglobin and total creatine kinase activity (total-CK) upon admission to the emergency room or within a short defined time interval after admission. Then, in accordance with the reflex algorithm, if a negative result is obtained for either of these two biochemical marker tests, the two biochemical marker tests are repeated approximately every four hours until there is a positive result, or until the test combination is run a predetermined number (e.g., four) of times. Should the test results always be negative, the testing cascade is finished with a Troponin I test because of its higher specificity and wider time window coverage: a positive result indicates that the patient should be treated for angina and minor myocardial damage; a negative result indicates that causes of chest pain unrelated to cardiac involvement should be considered. If there are any elevated values obtained for myoglobin and/or total-CK during the testing regimen described above, a creatine kinase MB (CKMB) mass test is performed. In the case of a positive result for both the CKMB mass test and a calculated relative index (RI %) of CKMB to total CK, no further testing is required, and an indication of acute AMI according to the World Health Organization criteria may be established. In the case of a negative result for the CKMB mass test, troponin I is measured for clarification. In all instances other than positive CKMB and positive RI %, the sequences specified according to the decision tree end with a Troponin I test as the final test. The cut-offs of the different markers used in the Reflex algorithm are not necessarily identical with the clinically-determined normal ranges and may be adjusted for optimal performance of the Reflex algorithm. The Reflex algorithm is preferably implemented on a computer system, including automated diagnostic systems, and may also be implemented as a computer program stored on a computer-readable medium. In accordance with yet another aspect of the present invention, in addition to determining the next most appropriate biochemical marker test, the Reflex algorithm of the present invention also serves as an Expert System by offering suggestions for clinically explaining the test results and/or recommendations for treatment and/or testing other than the specific sequence of biochemical marker tests needed to detect MI.

In accordance with a further aspect of the present invention, a system is provided which includes an immunoassay analyzer, a clinical chemistry analyzer, and a processor coupled to the immunoassay analyzer and to the clinical chemistry analyzer. The processor commands the immunoassay analyzer and clinical chemistry analyzer to execute measurements specified by a program executed by the processor in order to facilitate diagnosis of a pathology according to a reflex algorithm which includes at least one immunoassay and at least one clinical chemistry assay.

The method and apparatus of the present invention, by providing a reflex algorithm for detecting AMI, facilitates unambiguous and early diagnosis of acute myocardial infarctions. Additionally, it not only aids in the determination of the appropriate biochemical tests that need to be run on a patient who presents chest pain or a suspected heart-associated condition but also, omits the execution of unnecessary assays while ensuring that all necessary combinations of laboratory results are covered. The reflex algorithm of the present invention, by selecting subsequent tests based upon the results of previously-run assays, automatically selects the appropriate biochemical markers for a given clinical situation, which concomitantly eliminates the need for human decision-making in selecting the tests, and minimizes the number of necessary tests that have to be run, thus leading to a faster and more reliable diagnosis of AMI. Such features are tantamount to diagnostic efficiency and cost effectiveness.

BRIEF DESCRIPTION OF THE DRAWINGS

Additional aspects, features, and advantages of the invention will be understood and will become more readily apparent when the invention is considered in the light of the following description made in conjunction with the accompanying drawings, wherein.

DETAILED DESCRIPTION OF THE INVENTION

Figure 1A:
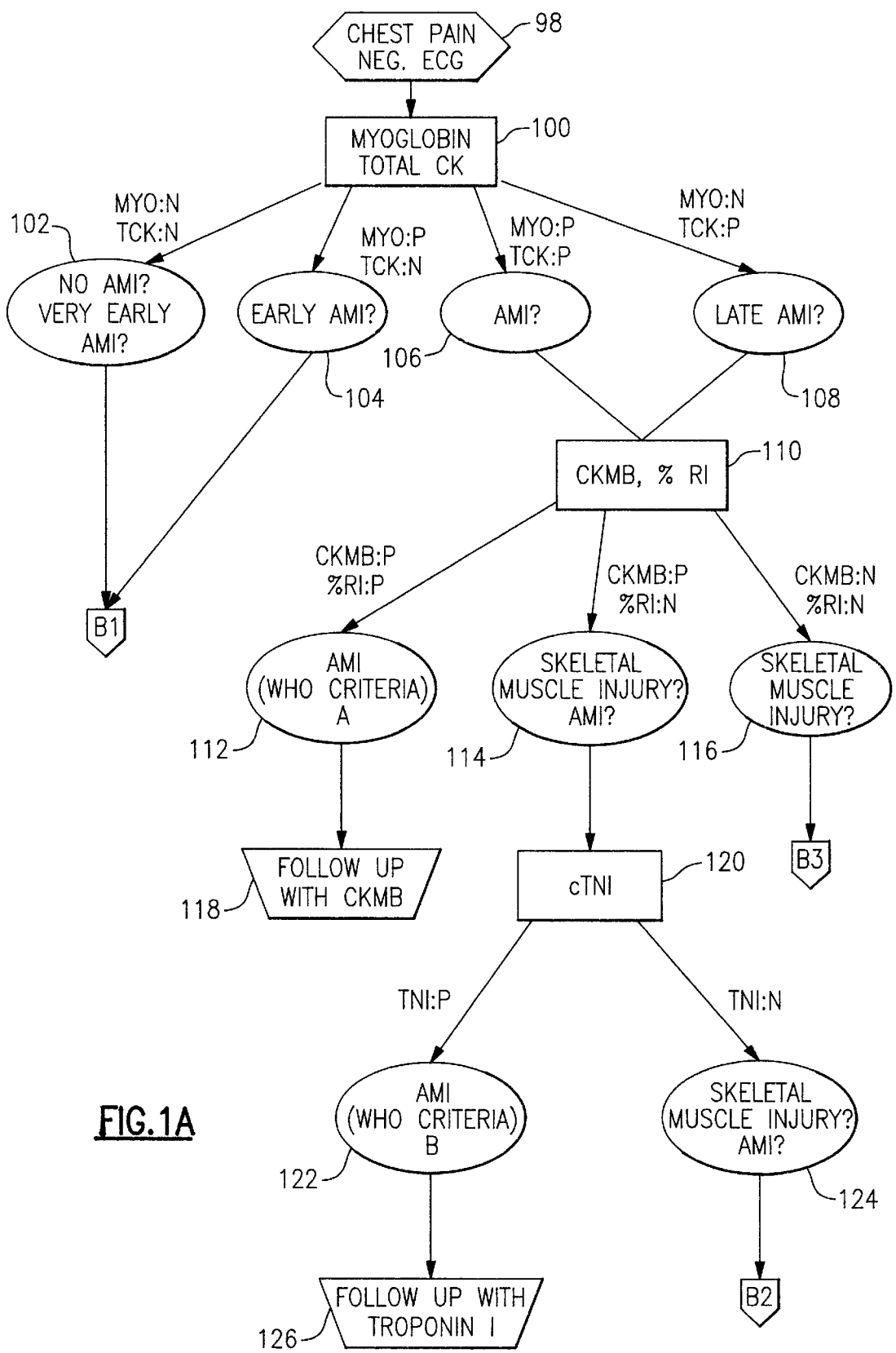
FIGS. 1A–1F schematically depict a decision tree of an illustrative Reflex algorithm for detecting myocardial infarction in accordance with an embodiment of the present invention.
Figure 1B:
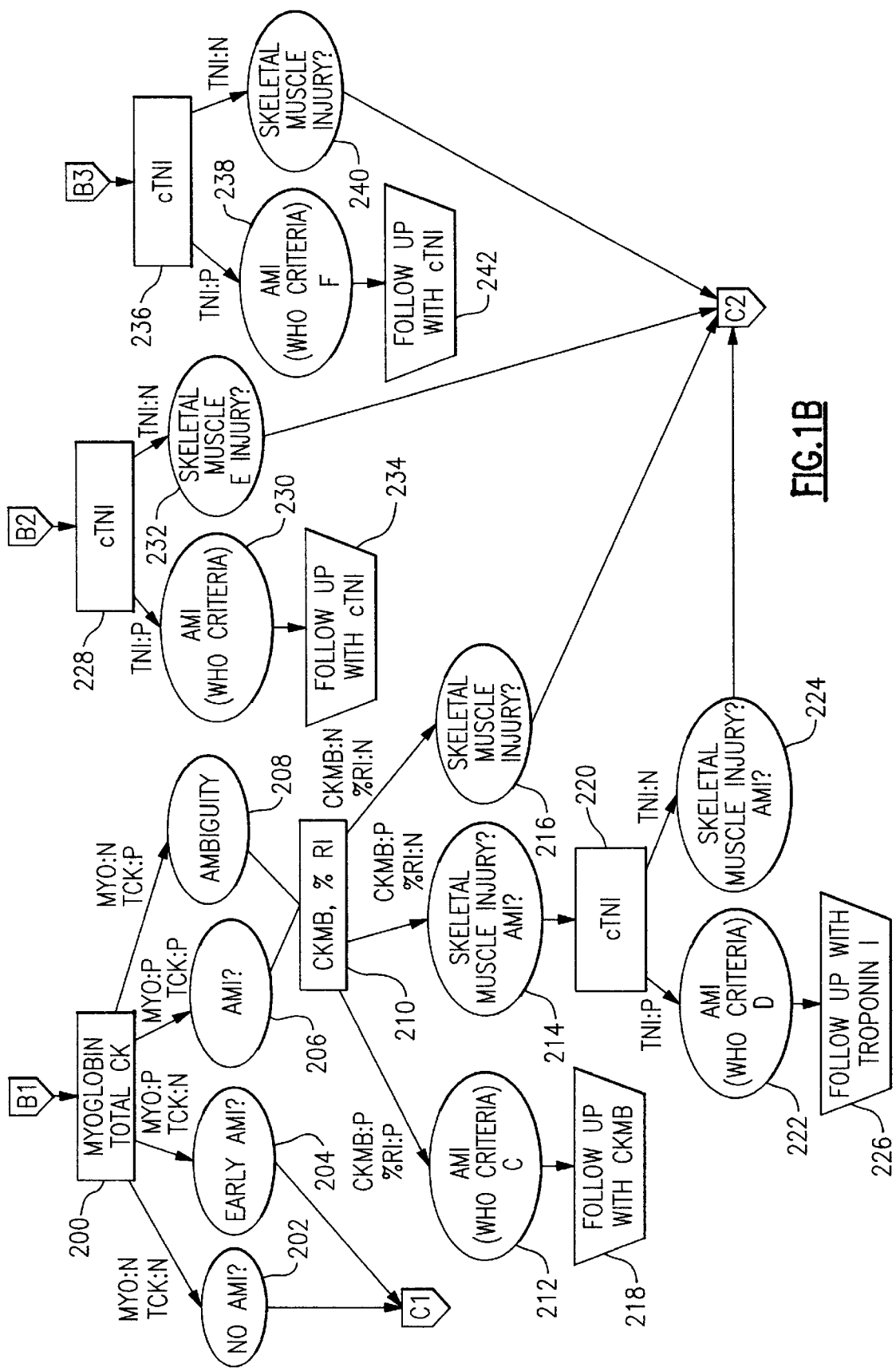
Figure 1C:
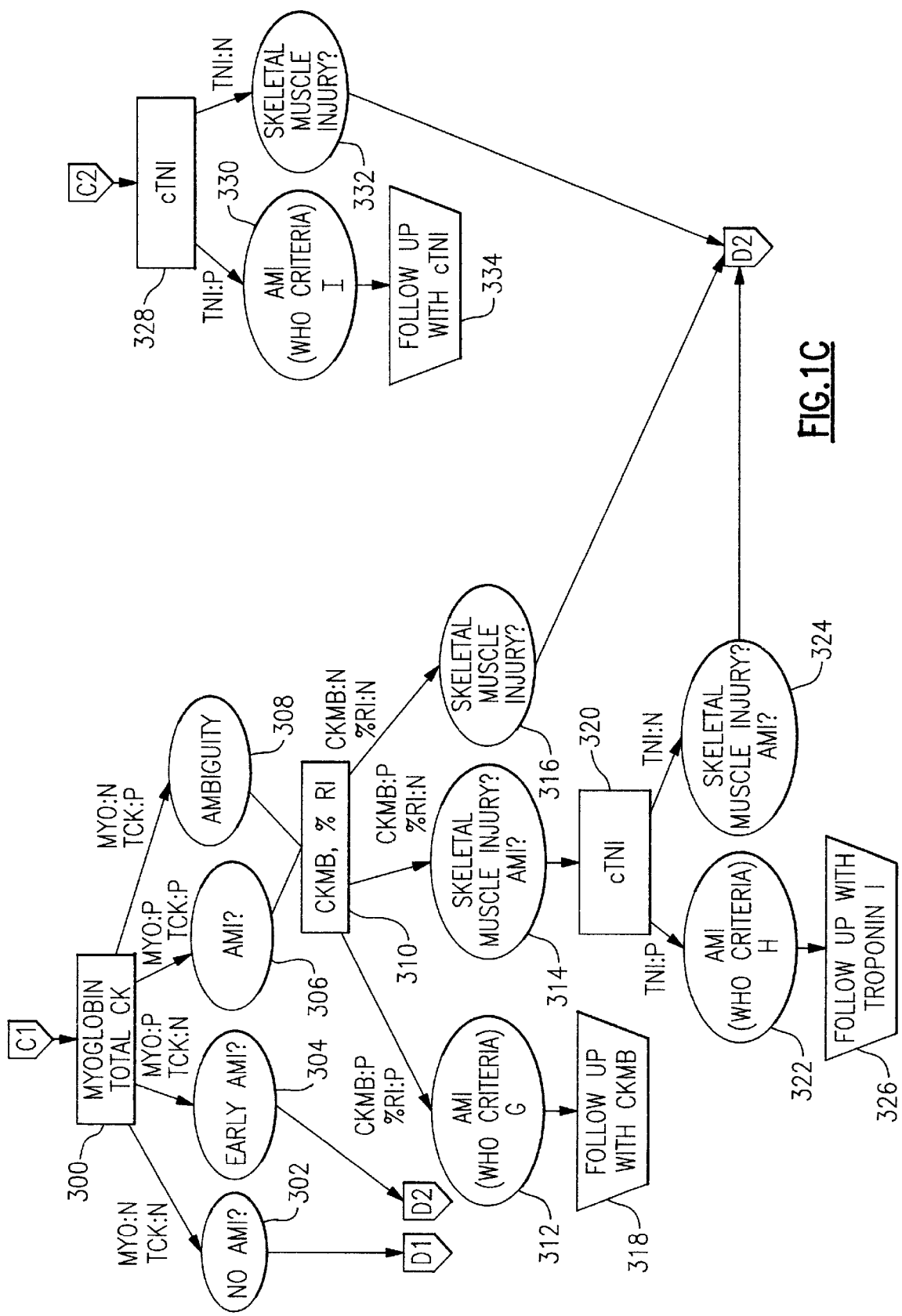
Figure 1D:
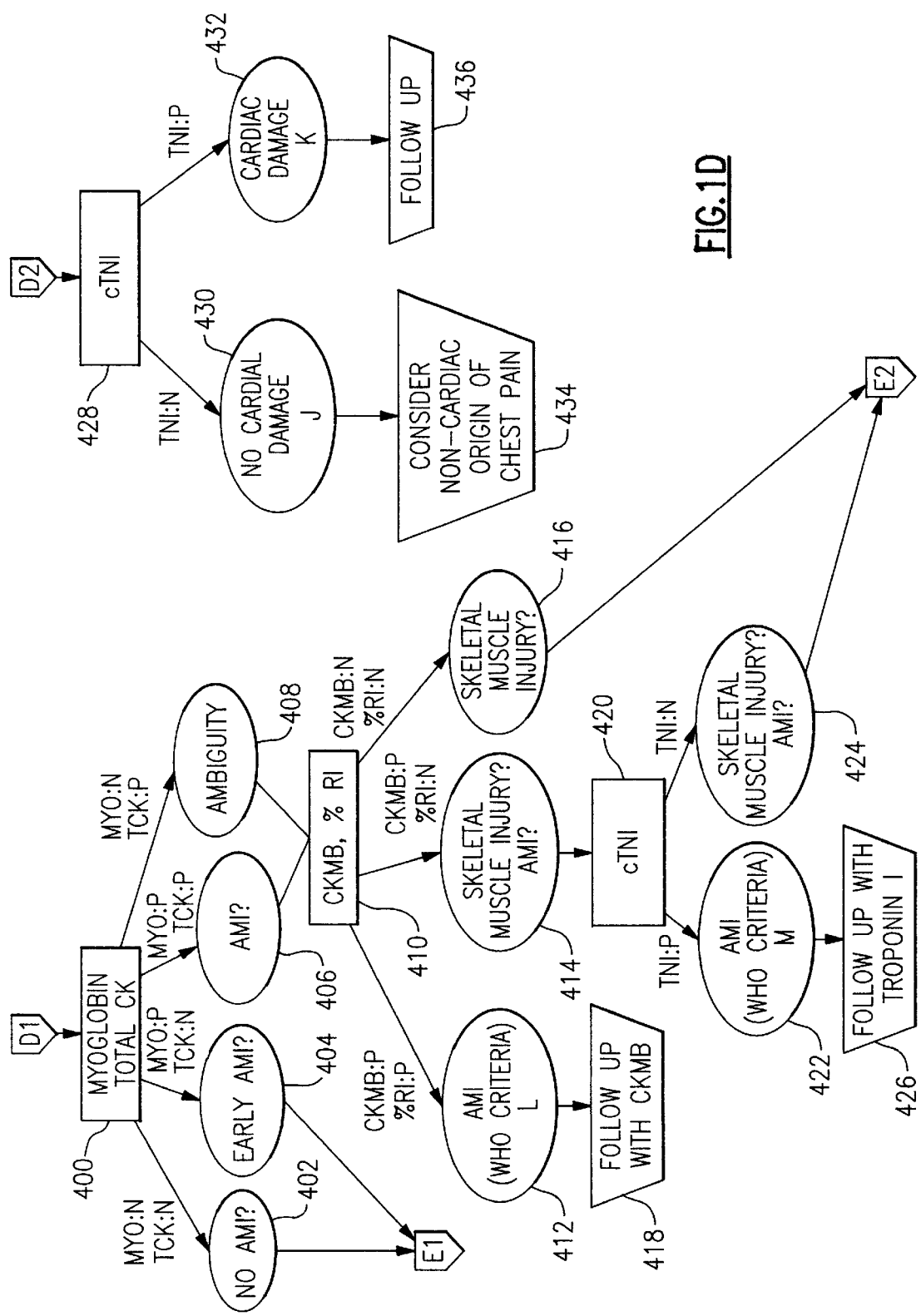
Figure 1E:
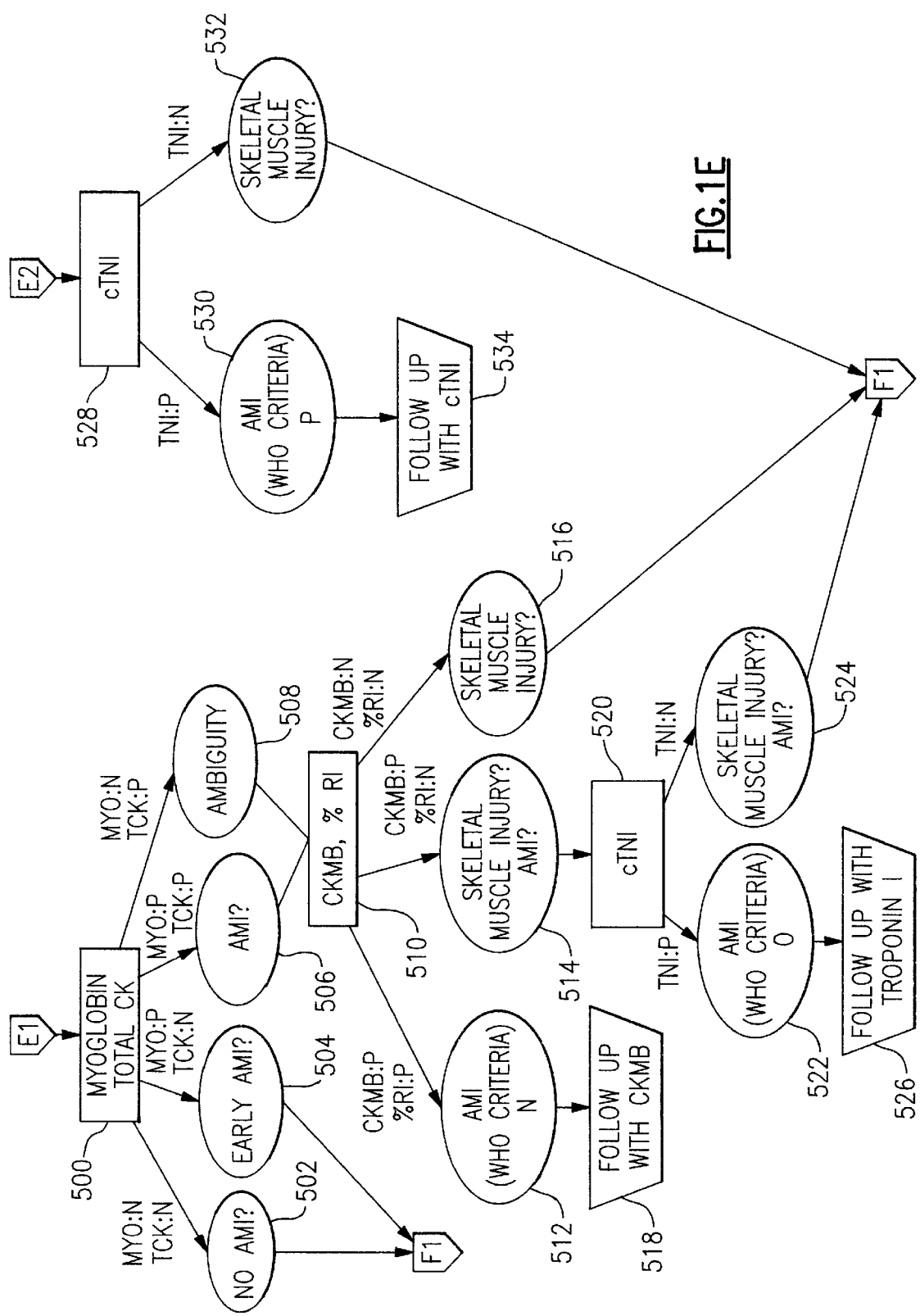
Figure 1F:
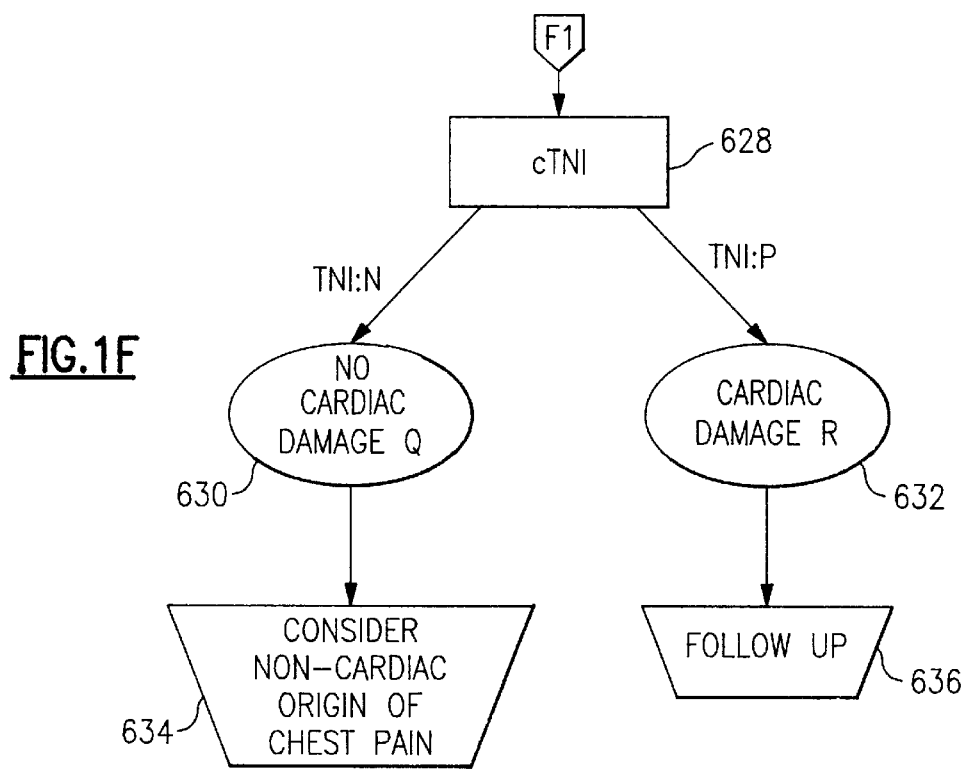

Referring generally to FIGS. 1A–1F, there is shown an operational flow or state diagram for a Reflex algorithm in accordance with an embodiment of the present invention. The depicted Reflex algorithm represents a decision tree, or hierarchical organization, of biochemical marker measurements, including both immunochemistry and clinical chemistry assays in which the markers have different appearance kinetics influencing their sensitivities and specificities within different time windows. More specifically, the illustrative Reflex algorithm of FIGS. 1A–1F employs myoglobin, total creatine kinase (tCK or total CK) activity, creatine kinase MB (CKMB) mass, and cardiac troponin I (cTNI) biochemical marker measurements. It is known that myoglobin has early sensitivity to myocardial infarction (about 2–3 hours post infarction), while its level returns to normal within about 24 hours, whereas total CK is elevated about 6 to 48 hours post-infarction and peaks about 18 hours after the onset of symptoms. Both myoglobin and especially total CK are relatively inexpensive, but are also non-specific to the myocardium. Troponin I is very specific but appears in the circulation later, and is relatively expensive compared to myoglobin or total CK. The optimum sensitivity for Troponin occurs at about 5–48 hours post-infarction. CKMB has a specificity less than that of Troponin I but greater than that of myoglobin and total CK, and has a sensitivity time window of about 5–48 hours post-infarction.

For clarity of exposition, as will be more fully understood hereinbelow, as depicted in FIGS. 1A–1F, rectangular shapes indicate assay execution steps (i.e., one or more biochemical marker measurements), elliptical nodes identify provisional or final patient status indications depending respectively on whether or not they are followed by an additional biochemical marker measurement step (i.e., indicated by a rectangle), trapezoidal nodes indicate suggested treatments and/or follow-up procedures based on the diagnostic endpoint (i.e., the final patient status indication) and preferably also on the sequence of foregoing test results which lead to the endpoint. It is noted that the elliptical nodes which are followed by another assay execution step (i.e., the provisional indications) do not represent steps which are necessarily indicated in practicing the Reflex algorithm, but are shown for clarity in describing the underlying logical structure and arrangement of the operational flow. As will be more fully understood below, however, such provisional indications may be provided as suggestions for clinically explaining the test results thus far obtained, and may also be associated with other suggested treatments or recommendations to the physician. It is also noted that all biochemical marker measurements or assays identified in each of FIG. 1A, FIG. 1B, FIG. 1C, FIG. 1D, FIG. 1E, and FIG. 1F are executed on blood drawn, in order, upon admission (e.g., within about three hours of admission), and in four hour increments subsequent to the time of the initially drawn blood upon admission (i.e., FIG. 1D and FIG. 1E corresponding to 12 hours and 16 hours post-admission, respectively). In addition, for simplicity, reference to blood, blood sample, or the like being used for a biochemical marker measurement, is generically used to refer to using whole blood, serum, or plasma as appropriate for the assay conducted.

Referring now more specifically to FIGS. 1A–1D, upon admitting a patient complaining of chest pain and/or demonstrating an abnormal (i.e., negative) electrocardiogram (ECG) measurement (step 98), both myoglobin and total creatine kinase (total CK) assays are run on blood samples drawn from the patient at that time (step 100), which is preferably as soon as possible. Initially testing both myoglobin and total-CK is effective in detecting recent (e.g., 2–3 hours post-onset) as well as older (e.g., 5–48 hours post-onset) infarctions.

If in step 100, the total CK measurement produces a positive result (indicated tcK:P; "positive" total CK meaning that total CK activity is above some threshold level), indicating the possibility of AMI (step 106) or the possibility of progressed AMI (i.e., late AMI, step 108), then in step 110 a creatine kinase MB measurement (CKMB) is performed using the first blood sample, and the percentage relative index (% RI) represented by the ratio of CKMB to total CK (using the total CK measurement for the first blood sample) is calculated. If the CKMB concentration is above a threshold level (i.e., positive, indicated as CKMB:P) and % RI is above a threshold (i.e., positive, indicated as % RI:P), then AMI, consonant with the World Health Organization definition, is indicated as the diagnosis of cardiac status for the patient (step 112), and preferably a follow-up CKMB measurement is suggested to the physician (step 118). Alternatively, if in step 110 the CKMB concentration is negative and % RI is negative (i.e., CKMB:N, % RI:N), indicating a possible skeletal muscle injury causation (step 116), then to further titrate the diagnosis and more specifically assess cardiac status, the flow proceeds via step 236 wherein the concentration of cardiac troponin I (cTNI) is measured for blood drawn about four hours after the first blood sample was drawn. If, however, in step 110 the CKMB concentration is positive and % RI is negative (i.e., CKMB:P, % RI:N), indicating a possible AMI or possible skeletal muscle injury causation (step 114), then cTNI is measured for the first blood sample (step 120). If in step 120 cTNI is positive, then AMI, consonant with the World Health Organization definition, is indicated as the diagnosis of cardiac status for the patient (step 122), and preferably a follow-up troponin I measurement is suggested to the physician (step 126). Alternatively, if in step 120 cTNI is negative (i.e., TNI:N), indicating a possible skeletal muscle injury causation (step 124), then to further titrate the diagnosis and more specifically assess cardiac status, the flow proceeds to step 228 wherein the concentration of troponin I is measured for blood drawn about four hours after the first blood sample was drawn.

It is appreciated that in accordance with the present invention, the illustrative embodiment of FIG. 1A provides possible pathways (i.e., a pathway representing a series of biochemical marker measurement steps performed according to the Reflex method, also referred to herein as a thread or sequence) for early detection of AMI as represented by the two diagnostic endpoints indicative of AMI (i.e., steps 112 and 122) which result from biochemical measurements on blood drawn upon admission only and do not require further blood samples that may be needed to diagnosis cardiac status in other patients according to the Reflex method.

Referring again to step 100, both tests indicating negative results (indicated as Myo:N, tcK:N; "negative" total CK meaning that total CK activity is below some threshold level; "negative" myoglobin meaning that myoglobin blood concentration is less than some threshold level) suggests that AMI is either not present or in its very early stages (step 102). Similarly, a positive myoglobin result (i.e., indicating a myoglobin blood concentration greater than a threshold level) and negative total CK result suggests that AMI may be in its early stages (step 104) because, as described, the myoglobin assay has its greatest sensitivity earlier than that of the total CK assay sensitivity. Since either of these cases in which initially measured total CK is negative may be due to the patient exhibiting early AMI, in either event an additional set of myoglobin and total CK tests are run (step 200) on blood drawn preferably about four hours after the time that the blood was drawn for the first set of myoglobin/total CK assays.

Referring now to steps 200–226, it is noted that these steps are directly analogous to hereinabove described steps 100–126, and thus will not be specifically described for purposes of brevity and clarity of exposition. As mentioned, biochemical marker measurements in steps 200–226 are preferably conducted on blood sampled about four hours after the first blood sample was drawn from the patient, steps 200–226 thus representing a measurement sequence corresponding to steps 100–126 but time delayed in order to identify, diagnose, and/or titrate delayed presentation of AMI relative to time of admission. It is also noted that if either (i) both CKMB and % RI are negative in step 210, or (ii) cTNI is negative in step 220, each case indicative of possible skeletal muscle injury (steps 216 and 224), then to further titrate the diagnosis and more specifically assess cardiac status, the flow proceeds to step 328 wherein the concentration of troponin I (cTNI) is measured for blood drawn about eight hours after the first blood sample was drawn. In addition, in step 200, similar to step 100, in either case where total CK is negative (steps 202 and 204), myoglobin and total CK will be measured on a subsequently drawn blood sample (step 300), which in this case is for blood drawn preferably about eight hours after the first blood sample (i.e., about four hours after the second blood sample). More specifically, if in step 200 either: (i) both tests indicate negative results (i.e., Myo:N, tcK:N), suggesting that AMI is not present (step 202) because there was no positive change in total CK (i.e., no increase in activity beyond the threshold) and myoglobin either remained or became negative, or (ii) myoglobin is positive and total CK is negative (Myo:P, tCK:N), suggesting that the patient may be in the early stages of AMI (step 204) because total CK remained negative and myoglobin remained or became positive, then in step 300 myoglobin and total CK is measured for blood drawn about eight hours after the first blood sample was drawn.

Referring to step 228, as mentioned, since a cTNI measurement of the first blood sample (i.e., step 120) did not indicate a level sufficient to indicate AMI, cTNI is measured for blood sampled about four hours after the first blood sample was drawn in order to further titrate a diagnosis. If in step 228 cTNI is positive, then AMI, consonant with the World Health Organization definition, is indicated as the diagnosis of cardiac status for the patient (step 122), and preferably a follow-up troponin I measurement is suggested to the physician (step 322). Alternatively, if in step 228 cTNI is negative (i.e., cTNI:N), indicating a possible skeletal muscle injury causation (step 124), then to still further differentiate a diagnosis and more specifically assess cardiac status with a statistically significant degree of certainty, the flow proceeds to step 328 wherein the concentration of troponin I is measured for blood drawn about eight hours after the first blood sample was drawn.

Referring to step 236, since for the first blood sample CKMB and % RI were both negative despite a positive cTNI measurement, cTNI is measured for blood sampled about four hours after the first blood sample was drawn in order to further assess the cause of elevated cTNI and to differentiate a diagnosis. If in step 236 cTNI is positive, then AMI is indicated as the diagnosis of cardiac status for the patient (step 238), and preferably a follow-up troponin I measurement is suggested to the physician (step 242). Alternatively, if in step 236 cTNI is negative (i.e., cTNI:N), indicating a possible skeletal muscle injury causation (step 240), then to still further differentiate a diagnosis and more specifically assess cardiac status with a statistically significant degree of certainty, the flow proceeds to step 328 wherein the concentration of troponin I is measured for blood drawn about eight hours after the first blood sample was drawn.

In step 328, if cTNI is positive, then cardiac damage which is possibly but not likely AMI is indicated as the diagnosis of cardiac status for the patient (step 330), and preferably a follow-up troponin I measurement is suggested to the physician (step 242). It is noted that the degree of cardiac damage may be further indicated, as well as different suggested treatments, based on the measured troponin I level (e.g., greater than 0.9 ng/ml indicating AMI rather than unstable angina). Alternatively, if in step 328 cTNI is negative (i.e., cTNI:N), still indicating a possible skeletal muscle injury causation (step 332), then to still further differentiate a diagnosis and more specifically assess cardiac status with a statistically significant degree of certainty, the flow proceeds to step 428 where the concentration of troponin I is measured for blood drawn about twelve hours after the first blood sample was drawn.

Referring now to step 300, which is performed if total CK activity was negative for both the first blood sample (step 100) and the blood sample drawn four hours after the first blood sample (step 200), if myoglobin and total CK measurements both produce negative results, then it is likely that no AMI is present (step 302) because the total CK activity never exceeded the threshold and the myoglobin concentration either decreased below threshold or never exceeded the threshold. Accordingly, in order to further differentiate the diagnosis and more specifically assess cardiac status, in step 428 the concentration of troponin I (cTNI) is measured for blood drawn about twelve hours after the first blood sample was drawn.

If, however, in step 300 the total CK measurement produces a positive result, indicating the possibility of AMI (step 306) or the possibility of progressed AMI (i.e., late AMI, step 308), then in step 310 a creatine kinase MB measurement (CKMB) is performed using the blood sampled at about eight hours after the first blood sample, and the percentage relative index (% RI) represented by the ratio of CKMB to total CK (using the total CK measurement for the eight-hour blood sample) is calculated. If the CKMB concentration is above a threshold level (i.e., positive, indicated as CKMB:P) and % RI is above a threshold (i.e., indicated as % RI:P), then AMI, consonant with the World Health Organization definition, is indicated as the diagnosis of cardiac status for the patient (step 312), and preferably a follow-up CKMB measurement is suggested to the physician (step 318). Alternatively, if in step 310 the CKMB concentration is negative and % RI is negative (i.e., CKMB:N, % RI:N), indicating a possible skeletal muscle injury causation (step 316), then to further differentiate the diagnosis and more specifically assess cardiac status, the flow proceeds to step 428 wherein the concentration of troponin I is measured for blood drawn about twelve hours after the first blood sample was drawn. If, however, in step 310 the CKMB concentration is positive and % RI is negative (i.e., CKMB:P, % RI:N), indicating a possible AMI or possible skeletal muscle injury causation (step 314), then cTNI is measured for the blood sample drawn about eight hours after the first blood sample was drawn (step 320). If in step 320 cTNI is positive, then AMI, consonant with the World Health Organization definition, is indicated as the diagnosis of cardiac status for the patient (step 322), and preferably a follow-up troponin I measurement is suggested to the physician (step 322). Alternatively, if in step 320 cTNI is negative (i.e., TNI:N), indicating a possible skeletal muscle injury causation (step 324), then to further differentiate the diagnosis and more specifically assess cardiac status, the flow proceeds to step 428 wherein the concentration of troponin I is measured for blood drawn about twelve hours after the first blood sample was drawn.

Referring now to step 428, which, as may be understood from the foregoing, will be performed as a result of any one of multiple pathways unless terminated before, if the troponin I concentration exceeds a threshold, corresponding to a positive result (i.e., TNI:P), then cardiac damage is indicated (step 432) as a diagnosis, and preferably certain specific follow up procedures are recommended (step 436) (e.g., follow up visit for troponin I measurement). It is noted that the degree of cardiac damage may be further indicated, as well as different suggested treatments, based on the measured troponin I level (e.g., greater than 0.9 ng/ml indicating AMI rather than unstable angina). If, however, the troponin I measurement result is negative (i.e., cTNI:N), then no cardiac damage is indicated as the diagnosis (step 430), and it is recommended that the patient be treated for non-cardiac origin of chest pain (step 434).

Referring again to step 300, if myoglobin is positive and total CK is negative, indicating a possible early AMI (step 304), then yet a further myoglobin and total CK measurement is taken, using blood sampled at about twelve hours after the first blood sample was drawn (step 400). For purposes of brevity and clarity of exposition, the progression of each and every step within steps 400–426, steps 500–526, steps 528–534, and steps 628–636 are not described in detail because they directly correspond, in order, to the flow of steps 200–226, steps 300–326, steps 328–334, and steps 428–436 with the following distinctions. First, for corresponding biochemical marker measurement steps, the blood is drawn about eight hours later (e.g., steps 628–636 and steps 428–436 are performed on blood drawn about 20 hours and 12 hours, respectively, after the first sample was drawn). Second, whereas in step 300 a positive myoglobin result and a negative tCK result are followed by a myoglobin and total CK measurement on a later drawn blood sample in step 400 (i.e., initiating the time delayed pathways represented by steps 400–426, steps 500–526, steps 528–534, and steps 628–636), in step 500 a positive myoglobin result and a negative total CK are followed by a cTNI measurement, since troponin I has not been elevated (i.e., at a positive level) for measurements on blood sampled every four hours through sixteen hours.

It is understood that the time delayed measurement pathways following a measurement of positive myoglobin and negative tCK in step 300 are provided to ensure the possibility of properly diagnosing AMI in the event that the elevated myoglobin on blood sampled eight hours after the first blood was drawn is due to a delayed presentation of AMI relative to time of admission (i.e., early AMI). It may be further appreciated that since a measurement of positive myoglobin and negative tCK in step 300, after twelve hours, may be indicative of early AMI detection, in addition to specifying a subsequent biochemical marker measurement step (i.e., step 400), in accordance with the present invention, not only may this provisional indication of early AMI be noted to a physician (corresponding to noting time of AMI onset) but also a recommendation of certain treatments to mitigate further cardiac damage may also be made to the physician.

More generally, throughout various points in the Reflex algorithm of FIGS. 1A–1F provisional indications (i.e., indicated by elliptical shapes), and possibly also certain recommended treatments or other clinical tests, may be noted to a physician as the measurements specified by the Reflex algorithm progressively are performed before an endpoint is reached. In addition, the indications and/or recommended treatments at a given point, including the endpoints, in the Reflex method may be not only dependent on the endpoint itself (i.e., characterized by at least one sequence of tests that result in the endpoint), but also further dependent on the specific pathway traversed (i.e., the specific sequence of tests performed and their results) thereto, since, as depicted, more than one pathway may lead to a common point in the flow. As an example of endpoint-dependent recommendation, an early diagnosis of AMI within the four hour time window may be suggestive of invasive treatment (e.g., enzymatic lysis or rescue PTCA), whereas later diagnosis of AMI (e.g., 12 hours) may be suggestive on non-invasive treatments. By way of example of specific-sequence-dependent diagnosis, consider that the indication and/or recommendation at step 330 preferably depends on whether it was reached via path 110→120→228→328 or path 200→210→328: the former path indicating AMI as very likely because CKMB was elevated, the latter path indicating a reasonable likelihood of unstable angina because CKMB was not elevated. In this respect, it is appreciated that the Reflex method provides for an Expert system for assessing and treating patients with possible cardiac damage. Such an Expert system may also draw upon additional patient information, such as patient medical history, other clinical tests performed since admission, and family history, preferably stored in a database, in order to provide a diagnosis and/or a treatment recommendation.

It may be appreciated that in accordance with the present invention, the illustrative embodiment of FIGS. 1A–1F provides possible pathways for detection of AMI or cardiac damage without requiring that all blood samples included in the overall Reflex method be drawn. More specifically: two diagnostic endpoints are provided based only on blood drawn upon admission (i.e., steps 112 and 122); four diagnostic endpoints are provided based only on blood drawn upon admission and four hours later (i.e., steps 212, 222, 230, and 238); three diagnostic endpoints are provided based only on blood drawn upon admission, and four and eight hours later (i.e., steps 312, 322, and 330); four diagnostic endpoints are provided based only on blood drawn upon admission, as well as four, eight, and twelve hours later (i.e., steps 412, 422, 430, and 432); three diagnostic endpoints are provided based only on blood drawn upon admission, as well as four, eight, twelve, and sixteen hours later (i.e., steps 512, 522, and 530); and only two endpoints (i.e., steps 630 and 632) are provided based on all blood samples included in the overall Reflex method (i.e., blood drawn every four hours up through twenty hours after the first sample was drawn).

As may be more fully appreciated in view of the foregoing description of FIGS. 1A–1F, the design of such a Reflex method for detecting AMI is based on sequencing biochemical marker measurements having various sensitivity, specificity, and appearance kinetics in such a manner so as to include pathways that: (i) result in an indication of no cardiac damage with a high degree of confidence (i.e., small probability of false negative), and (ii) result in an indication of AMI without always requiring that measurements be made on blood sampled for all blood sampling times used in the Reflex method, while accounting for the possibility of various onset times of AMI relative to time of admission. As such, it is understood that many variations and alternative Reflex algorithm implementations are possible. For instance, other markers may be substituted for ones used in the Reflex algorithm of FIGS. 1A–1F; for example, glycogen phosphorylase or heart-type fatty acid binding protein may be substituted for myoglobin, or Troponin T may be substituted for Troponin I. In addition, alternative Reflex algorithms may be designed and implemented using any of myriad other biochemical markers having various sensitivity, specificity, appearance kinetics, and costs, including for example: myoglobin, total creatine kinase, creatine kinase MB, troponin T, troponin I, glycogen phosphorylase BB, lactate dehydrogenase, heart-type fatty acid binding protein (h-FABP), carbonic anhydrase III, actin, myosin, and creatine kinase MB isoforms.

In addition, the design of such a Reflex method may also consider other factors, such as the associated monetary cost of the different biochemical marker measurements, time of blood sampling, and assay threshold levels. For instance, in the Reflex algorithm of FIGS. 1A–1F, troponin I measurements could replace CKMB measurements if cost were not a consideration; however, since troponin I is relatively expensive, CKMB measurements are implemented in various pathways (e.g., lower risk) to further differentiate a diagnosis such that a troponin I measurement may not be necessary. Generally, the times at which the patient's blood is drawn are selected in accordance with the preferred times (e.g., based on time-dependent sensitivity) for the various assays, as known from established testing procedures. Standard thresholds/levels (e.g., from the published literature)

may be implemented for the different assays used; however, as may be further understood below, the thresholds preferably may be adjusted to optimize diagnosis (e.g., a more conservative threshold to minimize false negatives) for a given Reflex algorithm decision tree structure.

Accordingly, it is appreciated that myriad variations of the illustrative Reflex algorithm depicted in FIGS. 1A–1F are possible, as well as myriad alternative Reflex algorithm implementations in accordance with the present invention. In any event, once a preliminary Reflex algorithm is designed according to these principles and criteria, its efficacy in classifying cardiac patients may be assessed by clinical testing of patients using each and every assay employed in the algorithm (and perhaps other tests as well), and comparing the classification using the designed Reflex algorithm to the results indicated by all the tests. An important factor is avoiding any false negative results or other mis-classification which would adversely affect patient classification, diagnosis, and treatment. By analyzing these results, it may be understood how the preliminary Reflex algorithm should be, if at all, modified in order to enhance classification (e.g., adding additional testing steps to certain branches of the algorithm and/or adjusting certain threshold levels, such as increasing a threshold level to avoid false negatives) and/or efficiency (e.g., eliminating certain steps of a branch in the algorithm and/or adjusting certain threshold levels). It is noted that for the threshold levels used in the illustrative embodiment represented in FIGS. 1A–1F, when total CK is positive it is not possible for CKMB to be negative and % RI to be positive.

Figure 2:
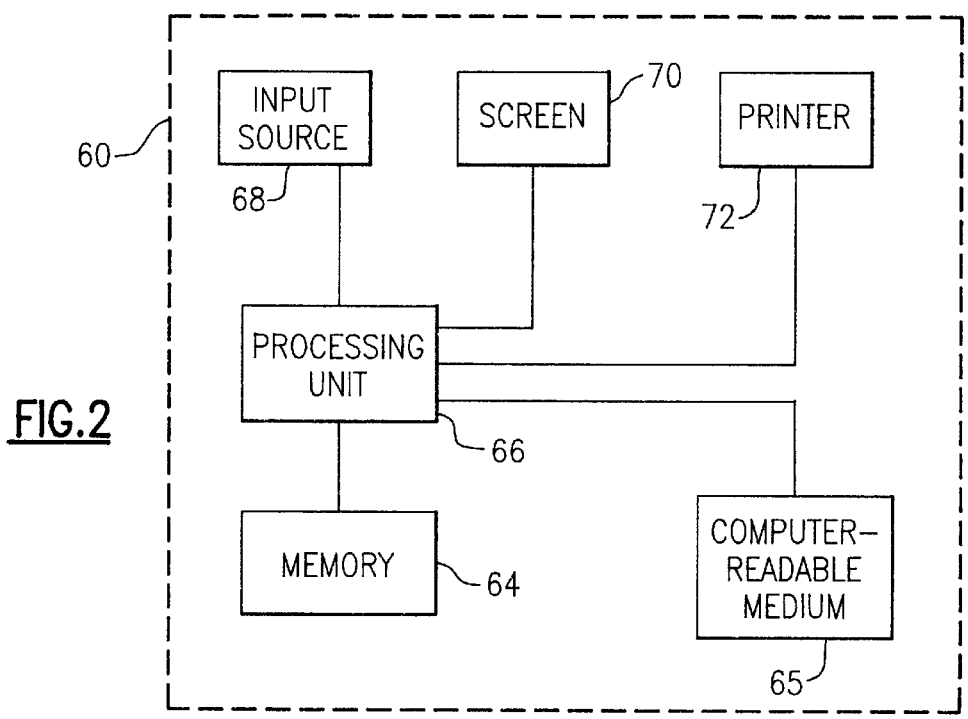
FIG. 2 schematically depicts a functional block diagram of an illustrative computer system used to implement a Reflex algorithm for detecting myocardial infarction in accordance with an embodiment of the present invention.

In accordance with an embodiment of the present invention, an AMI Reflex method such as that illustrated in FIGS. 1A–1F is preferably implemented programmatically in a processing system. It is appreciated that there are myriad processing system arrangements as well as programming paradigms for implementing the AMI Reflex method. For example, in a relatively simple arrangement, FIG. 2 illustrates a conventional digital computer system 60, comprising processing unit 66 coupled to memory 64 (e.g., RAM), another computer-readable medium 65 (e.g., flash memory, magnetic hard-drive, CD-ROM, etc.), an input device 68 (e.g., a keyboard and/or mouse and/or digital data input port), and output devices such as display 70 and printer 72, and wherein computer system 60 implements an AMI Reflex algorithm (e.g., the algorithm depicted in FIGS. 1A–1F) by stored-program execution. For instance, input device 68 implemented as a keyboard may be used by an operator to input results from one or more biochemical marker measurements, the input results then undergoing processing by program control of processing unit 66 in accordance with the AMI Reflex method, and subsequent biochemical marker measurement steps, diagnoses, and/or treatment recommendations specified by the AMI Reflex method according to such processing being output to display 70 and/or printer 72. It is understood that digital computer system 60 may also have access to a patient database (e.g., stored on computer-readable medium 65, or via a network to which computer system 60 has access) which includes other information to facilitate diagnosis or treatment.

In somewhat more detail, in such an implementation, for each identifiable patient the processor 66 executes the AMI Reflex algorithm in order to determine one or more biochemical marker measurements to be performed, and prompts an operator (e-g., via display 70) to execute the determined one or more biochemical marker measurements. After executing the measurements on an immunoassay analyzer (e.g., Immuno I, manufactured by Bayer Corporation) and/or on a clinical chemistry analyzer (e.g., OpeRA, manufactured by Bayer Corporation), the operator inputs the results of the measurements for the patient into the processing system via, for example, the keyboard and/or mouse 68. In response to such input, the processing system specifies either an additional biochemical marker measurement(s) for execution or an indication of the patient's myocardial status (e.g., a diagnosis when the input is associated with the final biochemical marker measurement(s) of a measurement sequence). In addition, at various points during execution of the Reflex algorithm, the processing system may indicate suggested additional tests or treatments to be conducted and/or suggestions for clinically explaining the test results. More specifically, by way of example, if the early stages of myocardial infarction are provisionally detected (e.g., based on the progression along a certain sequence of biochemical marker tests) before completing a full sequence of biochemical measurements, the processing system may, in addition to specifying subsequent biochemical marker tests to be executed for further titrating cardiac status, recommend certain treatments to mitigate further cardiac damage.

For the system of FIG. 2, various data structures or programming paradigms may be used to programmatically implement the AMI Reflex method and user interface. For example, the overall decision tree structure of FIGS. 1A–1F may be implemented as a hierarchy of downwardly linked list of records, each record having associated fields which may contain elements relating to provisional or final indications (e.g., indications shown in the ellipses) and/or provisional or final recommended treatments to be output to display 70 and/or printer 72, as well as pointers to other records in the list. As inputs are received via input device 68, a main program and/or various subroutines or modules use the inputs to identify an appropriate pointer to point to the next record, and appropriate subroutines or modules handle processing and/or outputting any appropriate information from the fields. In addition, the linked list may be further logically partitioned compared to the illustrative depiction in FIGS. 1A–1F such that indications and/or recommended treatments are more specifically dependent on the specific pathway traversed. In this illustrative programmatic implementation, the program and/or linked list data may be stored in memory 64 (e.g., RAM) and processing unit 66 (CPU) processes these signals to effect the AMI Reflex algorithm.

Figure 3:
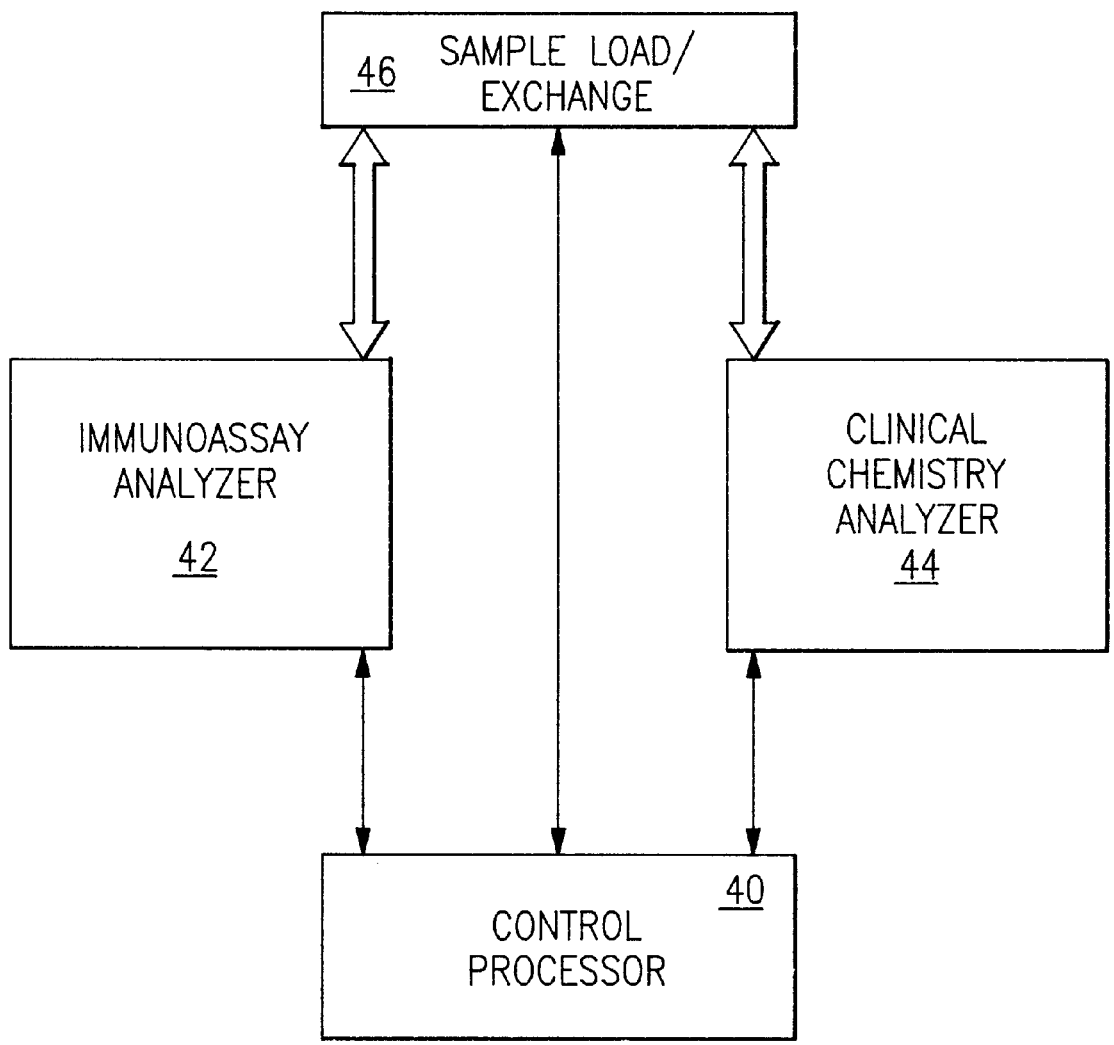
FIG. 3 shows a functional block diagram of an illustrative integrated system for implementing immunoassays and clinical chemistry assays according to a Reflex algorithm, in accordance with an embodiment of the present invention.

As may be appreciated, in an alternative embodiment depicted in FIG. 3, a control processor 40, such as digital computer system 60 of FIG. 2 or a microcontroller or microprocessor with any associated elements (e.g., memory, etc.), may be interfaced, by way of well known interfacing techniques, or otherwise integrated, with an immunoassay analyzer 42 and a clinical chemistry analyzer 44 to control and/or acquire data from assay test equipment. For example, immunoassay analyzer 42 may be an Immuno I manufactured by Bayer Corporation, and clinical chemistry analyzer 44 may be an OpeRA manufactured by Bayer Corporation, each interfaced to a personal computer or workstation which executes a program implementing the AMI Reflex algorithm (e.g., using PDC Concentrator software, from Technidata of France). It is understood that in such a system, the clinical chemistry analyzer and the immunoassay analyzer may run different samples (e.g., from different patients) concurrently in response to separate commands (e.g., writing into the respective loadlists of the analyzers) from processing system 40. Sample transfer between immunoassay analyzer and clinical chemistry analyzer may be implemented by a sample load/exchange system 46, which may be any of various known sample transfer mechanisms and systems (e.g., Labcell manufactured by Bayer, or Labinterlink manufactured by LabFrame of Omaha, Nebr.), shown under the control of control processor 40. It is understood that coupling of control processor 40 to sample load/exchange system 46, immunoassay analyzer 42, and clinical chemistry analyzer 44 may be implemented in various ways, such as dedicated buses or ports and/or shared buses or ports. Also, immunoassay analyzer 42 and clinical chemistry analyzer 44 may be operative in controlling sample exchange via sample load/exchange system 46.

It is understood that various processor arrangements may be implemented to provide an immunoassay analyzer and a clinical chemistry analyzer which are coordinately controlled according to an AMI reflex algorithm in accordance with the present invention, such that all tests may be specified and automatically executed without human intervention, other than the ministerial task of drawing additional blood samples that may be required as requested by the processing system implementing the AMI Reflex algorithm. For example, it is understood that the system of FIG. 3 may be implemented to closely integrate control processor 40 and the analyzers into a single instrument or platform, for example, by dedicating the control processor to the analysis equipment, each analyzer having its own processor. Alternatively, a single processor (e.g., control processor 40) may directly control both analyzers, with the analyzers not having their own local processors. In yet another alternative implementation, the AMI Reflex algorithm may be executed cooperatively on only two processors, each dedicated to one of the analyzers, with a sample transfer system between the analyzers. In a further alternative implementation, the immunoassay and clinical chemistry analyzers may have their own processors and be networked with one or more control processors or servers via a private network (e.g., a local area network (LAN), or a private wide area network (WAN)), or via a public network (e.g., Internet, WAN, or public-switched telephone network dial-up) to provide a public network-based Reflex algorithm service.

As mentioned, each analyzer may have its own, dedicated (e.g., local) processor, and a third control processor may coordinate overall processing according to the AMI Reflex method for the samples; such an implementation may employ various multiprocessing or parallel processing architectures or paradigms. By way of a simple example, a master/slave implementation may be employed, with the third control processor being the master, the two local processors being slaves. In such an implementation, it is understood that programmatic implementation of the Reflex algorithm may be distributed in various ways between control and each local processor. For example, for a given sample, the control processor may explicitly command each biochemical marker measurement for each analyzer in accordance with the AMI Reflex algorithm, and the local processors each controlling all the steps required to complete the specified measurement (e.g., sample and reagent handling, marker concentration measurement, etc.). Alternatively, the respective local processors may be programmed to execute, in response to a single command or message from the control processor, subroutines or subsequences of the Reflex algorithm which include a series of measurement steps that are of the respective type measured on the analyzer (i.e., clinical chemistry assay or immunoassay), and the control processor may maintain overall coordination between the analyzers for branches between immunoassays and clinical chemistry assays for the various pathways of the AMI Reflex algorithm. As various such branch points are encountered by the local processor (e.g., either at some point within the subroutine as conditioned on the results of biochemical marker measurement(s), or at the end of a subroutine) of the analyzer processing a given sample, the local processor may communicate a message to the control processor (e.g., using an interrupt request) indicative of the branch point, and the control processor can appropriately communicate a message to the other analyzer as to which as to what measurement or subroutine should be executed on the sample (or take other appropriate action, such as provide a final diagnosis and treatment recommendations).

As also mentioned, in an alternative implementation, analyzers and control processors or servers may be coupled over a network. It is understood that in such a system, for example, the AMI Reflex method may be an application implemented by a server, and AMI Reflex method data may also be written into a patient database (e.g., directly from the automatic assay testing equipment). Alternatively, an integrated automatic diagnostic combined immunoassay/clinical chemistry assay analyzer system may be implemented as a node on the network, and have access to other network resources such as patient databases. Such a network implementation is well-suited for implementing an Expert system.

For each of these illustrative implementations, the AMI Reflex algorithm may be implemented according to various programming paradigms or data structures, some of which have been described by way of example for a particular implementation. For example, the program may be generally structured according to a hierarchical downward linked list of files. Also, the Reflex algorithm may be partitioned or distributed between or among dedicated processors for the immunoassay and clinical chemistry analyzers and a control processor in communication with the dedicated processors. In addition, each of these systems may be implemented as Expert Systems. As noted, the Reflex algorithm may be implemented to provide additional treatment or testing recommendations based on the specific progression of results along a measurement path (also referred to herein as sequence or thread). To further enhance diagnostic efficacy of such an Expert system, the processing systems may also have access to additional patient data (e.g., via a database), such as patient medical history, family history, results from additional tests performed (e.g., electrocardiogram analysis) since admission, etc., and diagnosis and/or treatment recommendations may also account for such information. Of course, such an Expert system may be implemented off-line and/or on a network by a processor which is independent of the analyzers or control processor, and which has access to AMI Reflex method results and other patient data (e.g., coupled to a patient database to which Reflex method testing results are written).

It is further appreciated that a Reflex algorithm for AMI is only one of myriad possible reflex-type algorithms that may be developed for implementation by the foregoing illustrative systems which include both an immunochemistry analyzer and a clinical chemistry analyzer under control of at least one processor implementing a reflex-type algorithm. For example, such a system may be employed to implement reflex-type algorithms that may be developed in order to diagnose other pathologies such as liver disease, lipid risk, or other pathologies where both immunoassays and clinical chemistry assays are used. Further, it is understood that such a system may further integrate additional instrumentation to implement any further testing (e.g., hematology, urinalysis) required by the reflex algorithm.

The following example is meant to illustrate and exemplify various aspects of carrying out the present invention and is not intended to limit the invention.

EXAMPLE

The reflex algorithm in accordance with the present invention was evaluated and refined during a clinical trial at Hartford Hospital, Hartford, Conn., in which it was demonstrated that performance of the algorithm can reduce the number of tests performed on a patient by about 70%, compared with a testing scheme in which all markers were tested regardless of the outcome of previous tests. Other algorithms in the art suffer from the latter type of test scheme, which is more time consuming and costly than the novel reflex algorithm of the present invention.

The experiment comprised measurements of creatine kinase (tCK) activity, its MB isoenzyme (CKMB) as a mass assay, myoglobin, and cardiac troponin I (cTNI) for blood samples collected serially, upon admission and in four hour increments up through twelve hours post-admission, on patients presenting to the emergency room with a chief complaint of chest pain. Analysis of total CK was performed on a Technicon RA-XT whereas all other assays were performed on an Immuno 1 instrument (Bayer Corporation). The diagnostic results based on all such measurements were compared with the results provided by applying the Reflex algorithm of FIGS. 1A–1F to the measured data. In the Reflex algorithm, the cut-off (i.e., threshold) levels for Myoglobin, CKMB and Troponin I were used as recommended by the manufacturer of the test (i.e., Bayer in this case), and the cut-off level for t-CK was set at 100 U/L although the manufacturer recommends 130 U/L; this is to help to avoid false positive results during reflex testing. The cut-off for the % RI (Percent Relative Index) was set at 4%. For the purpose of this experimental study the data were run through the Reflex algorithm manually. It is noted that development of this illustrative Reflex algorithm considered the cost-effective use of cardiac markers for the emergency department evaluation of patients with chest pain.

Based on the results from the biochemical marker measurements, patients were categorized by the Reflex algorithm into one of eighteen possible endpoints (steps shown as including labels A–R in FIGS. 1A–1F) in the Reflex algorithm. Diagnoses for: endpoints A and B would require only the first sample at the time of admission; endpoints C, D, E and F would require only the first blood sample and an additional blood sample drawn 4 hours post-admission; endpoints G, H and I would require blood samples drawn up through 8 hours post-admission; endpoints J, K, L, M would require blood samples drawn through 12 hours post-admission; endpoints N, 0 and P would require blood samples drawn up through 16 hours post-admission; and endpoints Q and R would require blood samples drawn through 20 hours post-admission.

The distribution of patients with AMI (sample size of n=34), as determined from all biochemical marker measurements, reaching various endpoints according to application of the Reflex algorithm was as follows: A =52.94%; B=11.76%; C=17.64%; E=2.94%; F=11.76%; I=2.94%. All the patients in non-AMI group (n=67) reached endpoint J, 12 hours post-admission. Notably, no diagnosis required any samples drawn beyond 12 hours post-admission, which represents the unlikelihood of a patient having a positive myoglobin result and a negative total CK result at 8 hours post admission after demonstrating negative total CK upon admission and four hours later. Nevertheless, provision of such a pathway in the illustrative Reflex algorithm is useful to diagnose detecting the possibility of early AMI beyond four hours post-admission.

The experimental results therefore show that 64.70% of AMI cases were diagnosed using the Reflex algorithm with only the first sample at admission, 32.34% with the first sample at admission and a sample drawn about 4 hours later, and the remaining 2.94% with the first sample at admission as well as samples drawn 4 hours and 8 hours post-admission. For this entire sample of patients (i.e., both AMI and non-AMI), using only the Reflex algorithm for diagnosing myocardial status would have reduced the number of tests from 1616 if all markers were tested to 589. It is noted that this reduction in the number of tests required to diagnose AMI according to the Reflex algorithm is due, in part, to the hierarchical arrangement of tests such that normal results for myoglobin and total CK for the first two samples separated by about 4–6 hours obviates the need for CK, and abnormal results for myoglobin and CKMB may be sufficient to indicate presence of acute myocardial infarction without the need to perform cTNI.

The data thus clearly demonstrates that the illustrative Reflex algorithm of FIGS. 1A–1F according to the present invention is an efficient tool for proper utilization of cardiac markers in early detection of myocardial damage and can substantially reduce the cost by appropriate utilization of laboratory services.

As may be appreciated from the foregoing description, including the illustrative embodiment, the illustrative variations and modifications, and the example, and as may be further appreciated by practicing the present invention, the present invention provides myriad advantages and attendant advantages. For instance, a Reflex method according to the present invention not only helps determine the appropriate biochemical tests, but also eliminates unnecessary assays. Accordingly, it provides for a cost effective, unambiguous, and early diagnosis of acute myocardial infarctions and a stratification of risk for non-AMI patients, such as those with unstable angina pectoris. Since each step in the Reflex method is determined based solely on the results of a previous assay results, and all possible combinations of laboratory results are covered, no human decision making is required and the Reflex method is thus well suited for ministerial operator implementation, and particularly well suited for programmatic implementation, and more particularly well suited for incorporation into the software of automated diagnostic platforms which do not require any operator intervention. It was also found that eliminating human decision making from test determination resulted in faster and more cost effective diagnosis of AMI.

Although the above description of illustrative embodiments of the invention, and various modifications thereof, provides many specificities, these enabling details should not be construed as limiting the scope of the invention, and it will be readily understood by those persons skilled in the art that the present invention is susceptible to many modifications, adaptations, and equivalent implementations without departing from this scope and without diminishing its attendant advantages. It is therefore intended that the present invention is not limited to the disclosed embodiments but should be defined in accordance with the claims which follow.

We claim:

1. A method for detecting myocardial infarction in an individual, comprising the steps of:

performing one of a plurality of sequences of biochemical marker measurement steps prescribed by a reflex algorithm, each of the biochemical marker measurement steps including measuring a concentration level or activity of at least one biochemical marker of myocardial infarction in a serum, plasma or whole blood sample obtained from said individual at one of a plurality of times from admission, each sequence of the reflex algorithm beginning with a common first biochemical marker measurement step conducted on a first serum, plasma or whole blood sample obtained from said individual within a first predetermined time from admission, each of the biochemical marker measurement steps subsequent to the common first step selectively performed based on results from a precedent biochemical marker measurement step, each sequence terminating in a respective final biochemical marker measurement step conducted on serum, plasma or whole blood sampled from said individual at one of a plurality of different times subsequent to admission; and providing an indication of myocardial infarction for said individual based on the sequence performed and on the results of the respective final biochemical marker measurement step.

2. The method according to claim 1, wherein each of said biochemical marker measurement steps measures at least one biochemical marker selected from the group consisting of myoglobin, total creatine kinase, creatine kinase MB, troponin T, troponin I, glycogen phosphorylase BB, lactate dehydrogenase, heart-type fatty acid binding protein (h-FABP), carbonic anhydrase III, actin, myosin, and creatine kinase MB isoforms.

3. The method according to claim 1 wherein said common first biochemical marker measurement step includes measuring a plurality of biochemical markers having different rates of appearance.

4. The method according to claim 1, wherein said common first biochemical marker measurement step includes measuring myoglobin and total creatine-kinase.

5. The method according to claim 4, wherein, for said common first biochemical marker measurement step, a creatine-kinase activity below a predetermined level results in measuring myoglobin and creatine-kinase for serum, plasma or whole blood sampled from said individual subsequent to said first predetermined time.

6. The method according to claim 4, wherein, for said common first biochemical marker measurement step, a creatine-kinase activity above a predetermined level results in measuring creatine kinase MB for serum, plasma or whole blood sampled from said individual at said first predetermined time.

7. The method according to claim 1, wherein the biochemical markers include immunoassays and clinical chemistry assays.

8. The method according to claim 1, wherein said step of providing an indication includes providing an indication of time since onset of infarction.

9. The method according to claim 1, wherein said step of providing an indication includes providing the indication based on the results of the biochemical marker measurements in the sequence performed, thereby depending on the specific sequence performed.

10. The method according to claim 1, wherein one or more points along said reflex algorithm indicates a recommended treatment or test other than the biochemical marker measurements within the sequences of the reflex algorithm.

11. The method according to claim 10, wherein the recommended treatment or test other than the biochemical marker measurements is provided subsequent to one or more of said respective final biochemical marker measurement steps.

12. The method according to claim 1, wherein specification of the sequence of biochemical marker measurements is implemented by a digital computer according to a stored representation of said reflex algorithm.

13. The method according to claim 12, wherein said digital computer provides output indicative of a recommended treatment or test other than the biochemical marker measurements treatment at one or more points along said reflex algorithm.

14. The method according to claim 13, wherein the recommended treatment or test other than the biochemical marker measurements is provided subsequent to one or more of said respective final biochemical marker measurement steps.

15. The method according to claim 1, wherein said plurality of different times subsequent to admission include said first predetermined time within admission, a second time about four hours subsequent to said first time, a third time about four hours subsequent to said second time, and a fourth time about four hours subsequent to said third time.

16. A computer-implemented method for detecting myocardial infarction in an individual, comprising the steps of:

performing one of a plurality of sequences of biochemical marker measurement steps prescribed by a reflex algorithm implemented on a computer, each of the biochemical marker measurement steps including measuring a concentration level or an activity of at least one biochemical marker of myocardial infarction in a serum, plasma or whole blood sample obtained from said individual at one of a plurality of times from admission, each sequence of the reflex algorithm beginning with a common first biochemical marker measurement step conducted on a first serum, plasma or whole blood sample obtained from said individual within a first predetermined time from admission, each of the biochemical marker measurement steps subsequent to the common first step selectively performed based on results from a precedent biochemical marker measurement step, each sequence terminating in a respective final biochemical marker measurement step conducted on serum, plasma or whole blood sampled from said individual at one of a plurality of different times subsequent to admission; and providing an indication of myocardial infarction for said individual based on the sequence performed and on the results of the respective final biochemical marker measurement step.

17. The method according to claim 16, wherein said computer outputs signals to at least one automated laboratory analyzer to control execution of at least one of the biochemical marker measurements.

18. The method according to claim 17, wherein said at least one automated laboratory analyzer includes a clinical chemistry analyzer and an immunoassay analyzer.

19. The method according to claim 17, wherein said at least one automated laboratory analyzer includes a plurality of analyzers linked by an automatic sample handling device that allows sharing of samples.

20. The method according to claim 17, wherein said at least one automated laboratory analyzer and computer are part of an integrated diagnostic system.

21. The method according to claim 16, wherein said reflex algorithm is represented as code or data stored on a computer-readable medium accessible to a processor associated with said computer.

22. The method according to claim 16, wherein said reflex algorithm is represented as a database stored on a computer-readable medium, and wherein a processor associated with said computer executes an application program to implement the reflex algorithm.

23. A diagnostic system comprising:

an immunoassay analyzer;

a clinical chemistry analyzer;

a processor coupled to said immunoassay analyzer and to said clinical chemistry analyzer, wherein said processor commands said immunoassay analyzer and clinical chemistry analyzer to execute measurements specified by a program executed by the processor in order to facilitate diagnosis of acute myocardial infarction according to a reflex algorithm which includes at least one immunoassay and at least one clinical chemistry assay.

24. The diagnostic system according to claim 23, further comprising a hematology analyzer coupled to said processor, and wherein said measurements specified by the program include a measurement executed by the hematology analyzer in response to a command from said processor.

25. The diagnostic system according to claim 23, wherein said immunoassay analyzer and said clinical chemistry analyzer each have a respective local processor in communication with said processor, wherein the local processors respectively control execution of measurements specified by said processor on the immunoassay and clinical chemistry analyzer.

26. The diagnostic system according to claim 25, wherein said local processors each independently and selectively execute a local program or subroutine to control a sequence of measurements in response to a command from said processor.

27. A system for specifying a sequence of biochemical marker measurement steps for using an immunoassay and a clinical chemistry analyzer to generate an indication of myocardial infarction, the biochemical marker measurement steps including measuring a concentration level or an activity of at least one biochemical marker of myocardial infarction in a serum, plasma or whole blood sample obtained from said individual at a predetermined time from admission, the system comprising:

means for storing information representing a reflex algorithm indicating a plurality of predetermined sequences of biochemical marker measurements;

means for receiving information concerning outputs from biochemical marker measurements conducted on the immunoassay analyzer and the clinical chemistry analyzer, and means for selectively specifying a biochemical marker measurement and for selectively specifying an indication of myocardial infarction according to the stored information in response to the information concerning outputs from biochemical marker measurements.

28. The system according to claim 27, wherein said receiving means is an input device used by an operator.

29. The system according to claim 27, wherein said receiving means is in communication with said immunoassay analyzer and said clinical chemistry analyzer for receiving said information concerning outputs.

30. The system according to claim 27, wherein said specifying means is in communication with said immunoassay analyzer and said clinical chemistry analyzer for commanding execution of the specified biochemical marker mesurement.

31. A system for specifying a sequence of biochemical marker measurement steps for using an immunoassay and a clinical chemistry analyzer to generate an indication of myocardial infarction, the biochemical marker measurement steps including measuring a concentration level or an activity of at least one biochemical marker of myocardial infarction in a serum, plasma or whole blood sample obtained from said individual at a predetermined time from admission, the system comprising:

a computer-readable medium that stores information that represents a reflex algorithm in which a plurality of predetermined sequences of biochemical marker measurement steps; and a processor that receives information concerning outputs from biochemical marker measurements conducted on the immunoassay analyzer and the clinical chemistry analyzer, and that selectively specifies a biochemical marker measurement and selectively specifies an indication of myocardial infarction according to the stored information in response to the information concerning outputs from biochemical marker measurements.

32. The system according to claim 31, further comprising an input device coupled to said processor and used by an operator to enter said information concerning outputs.

33. The system according to claim 31, wherein said processor is in communication with said immunoassay analyzer and said clinical chemistry analyzer to receive said information concerning outputs therefrom, and to send information indicative of a specified biochemical marker measurement to be executed thereto.

34. The system according to claim 33, wherein said immunoassay analyzer and said clinical chemistry analyzer each have a respective processor in communication with said processor.

35. The system according to claim 33, wherein said processor is coupled to said immunoassay analyzer and said clinical chemistry analyzer, and said processor communicates information to commands execution of the specified biochemical marker measurement.

36. The system according to claim 31, wherein said processor is in communication with said immunoassay analyzer and said clinical chemistry analyzer to send information indicative of a specified biochemical marker measurement to be executed thereto, and further comprising a patient database to which said immunoassay analyzer and said clinical chemistry analyzer write said information concerning outputs for a patient in response to respective tests executed thereby.

37. A system for detecting myocardial infarction in an individual, comprising:

means for specifying selective performance of one of a plurality of sequences of biochemical marker measurement steps prescribed by a reflex algorithm; and means for providing an indication of myocardial infarction for said individual based on the sequence performed and on the results of the respective final biochemical marker measurement step;

wherein each of the biochemical marker measurement steps includes measuring a concentration level or an activity of at least one biochemical marker of myocardial infarction in a serum, plasma or whole blood sample obtained from said individual at a predetermined time from admission, each sequence of the reflex algorithm begins with a common first biochemical marker measurement step conducted on a first serum, plasma or whole blood sample obtained from said individual within a first predetermined time from admission, each of the biochemical marker measurement steps subsequent to the common first step is selectively performed based on results from a precedent biochemical marker measurement step, each sequence terminates in a respective final biochemical marker measurement step conducted on serum, plasma or whole blood sampled from said individual at a respective one of a plurality of different times subsequent to admission.

38. The system according to claim 37, further comprising an immunoassay analyzer and a clinical chemistry analyzer each in communication with said specifying means, each selectively receiving from said specifying means a command for invoking a biochemical marker measurement.

39. A computer program embodied on a computer-readable medium, comprising:
   a code segment including a sequence of instructions to determine measurements to be executed by a clinical chemistry analyzer and an immunoassay analyzer according to a representation of a reflex algorithm; and
   a code segment to output an indication of myocardial infarction based on the executed measurements.

40. The computer program embodied on a computer-readable medium according to claim 39, wherein said representation of a reflex algorithm is stored on the computer-readable medium.

41. The computer program embodied on a computer-readable medium according to claim 39, further comprising a communication code segment including instructions to communicate with the immunoassay analyzer and the clinical chemistry analyzer.

42. The computer program embodied on a computer-readable medium according to claim 41, wherein said communication code segment includes instructions operative in sending to said immunoassay analyzer and said clinical chemistry analyzer commands to execute measurements.

43. The computer program embodied on a computer-readable medium according to claim 41, wherein said communication code segment includes instructions operative in receiving information concerning results from measurements executed by said immunoassay analyzer and said clinical chemistry analyzer.

44. A computer-implemented method for specifying a sequence of biochemical marker measurement steps for using an immunoassay and a clinical chemistry analyzer to generate an indication of myocardial infarction, the biochemical marker measurement steps including measuring a concentration level or an activity of at least one biochemical marker of myocardial infarction in a serum, plasma or whole blood sample obtained from said individual at one of a plurality of times from admission, the method comprising the steps of:
   storing information representing a reflex algorithm indicating a plurality of predetermined sequences of biochemical marker measurements;
   measuring a concentration level or an activity of at least one biochemical marker of myocardial infarction in a first serum, plasma or whole blood sample obtained from said individual within a predetermined time from admission;
   receiving information concerning outputs from biochemical marker measurements conducted on the immunoassay analyzer and the clinical chemistry analyzer; and
   selectively specifying a biochemical marker measurement to be executed on the immunoassay analyzer or the clinical chemistry analyzer based on the information concerning outputs and on the stored information representing a reflex algorithm; and
   specifying an indication of myocardial infarction according to the stored information in response to the information concerning outputs from biochemical marker measurements upon completing execution of one of the plurality of sequences.

* * * * *

UNITED STATES PATENT AND TRADEMARK OFFICE
CERTIFICATE OF CORRECTION

PATENT NO. : 6,099,469
DATED : August 8, 2000
INVENTOR(S) : Armstrong et al.

It is certified that error appears in the above-identified patent and that said Letters Patent is hereby corrected as shown below:

On the Title Page:
Item [54] "Infractions" should read --Infarctions--.
Item [56] Reference Cited, Other Publications:

"*Early Diagnosis Of Myocardial Infraction By Timed Sequential Enzyme Measurements*" should read --*Early Diagnosis Of Myocardial Infarction By Timed Sequential Enzyme Measurements*--.

"*Analysis Of The Clinical Variables Driving Decision In An Artificial Neural Network Trained To Identify The Presence of Myocardial Infraction*" should read --*Analysis Of The Clinical Variables Driving Decision In An Artificial Neural Network Trained To Identify The Presence of Myocardial Infarction*--.

Column 1, in the Title "Infractions" should read --Infarctions--
Column 13, line 2, "Labinterlink" should read --LabInterlink--
Column 16, line 18, "CK," should read --CKMB,--.

Signed and Sealed this

Twenty-fourth Day of April, 2001

*Attest:*

NICHOLAS P. GODICI

*Attesting Officer*      *Acting Director of the United States Patent and Trademark Office*